United States Patent
Dunkel et al.

(10) Patent No.: US 7,358,214 B2
(45) Date of Patent: *Apr. 15, 2008

(54) PYRAZOLYL CARBOXANILIDES FOR CONTROLLING UNWANTED MICROORGANISMS

(75) Inventors: Ralf Dunkel, Monheim (DE); Hans-Ludwig Elbe, Wuppertal (DE); Heiko Rieck, Ste Foy les Lyon (FR); Peter Dahmen, Neuss (DE); Ulrike Wachendorff-Neumann, Neuwied (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 475 days.

This patent is subject to a terminal disclaimer.

(21) Appl. No.: 10/543,210

(22) PCT Filed: Jan. 19, 2004

(86) PCT No.: PCT/EP2004/000344

§ 371 (c)(1),
(2), (4) Date: Jul. 22, 2005

(87) PCT Pub. No.: WO2004/067515

PCT Pub. Date: Aug. 12, 2004

(65) Prior Publication Data

US 2006/0089399 A1 Apr. 27, 2006

(30) Foreign Application Priority Data

Jan. 29, 2003 (DE) ................ 103 03 589

(51) Int. Cl.
*C07D 231/10* (2006.01)
*A01N 43/56* (2006.01)
*A61K 31/415* (2006.01)

(52) U.S. Cl. ........... 504/280; 548/356.1; 548/373.1; 548/374.1; 504/261; 514/403; 514/406

(58) Field of Classification Search ......... 548/356.1, 548/373.1, 374.1; 504/261, 280; 514/403, 514/406
See application file for complete search history.

(56) References Cited

U.S. PATENT DOCUMENTS

| | | | |
|---|---|---|---|
| 3,917,592 A | 11/1975 | Kobzina ............... 260/244 |
| 4,032,573 A | 6/1977 | Kaneko et al. ........ 260/562 N |
| 4,194,008 A | 3/1980 | Enders et al. .......... 424/322 |
| 5,223,526 A * | 6/1993 | McLoughlin et al. ... 514/406 |
| 5,416,103 A | 5/1995 | Eicken et al. ......... 514/355 |
| 5,914,344 A | 6/1999 | Yoshikawa et al. .... 514/406 |
| 5,922,732 A | 7/1999 | Urch et al. ............ 514/304 |
| 5,965,774 A | 10/1999 | Yoshikawa et al. .... 564/305 |
| 5,968,947 A | 10/1999 | Urch et al. ............ 514/299 |
| 6,093,726 A | 7/2000 | Urch et al. ............ 514/299 |
| 6,147,104 A | 11/2000 | Eicken et al. ......... 514/406 |
| 6,174,894 B1 | 1/2001 | Urch et al. ............ 514/299 |
| 6,177,442 B1 | 1/2001 | Urch et al. ............ 514/299 |
| 6,207,676 B1 | 3/2001 | Urch et al. ............ 514/304 |
| 6,291,474 B1 | 9/2001 | Brightwell et al. ..... 514/299 |
| 6,369,093 B1 | 4/2002 | Elbe et al. ............. 514/406 |
| 6,391,883 B1 | 5/2002 | Urch et al. ............ 514/255 |
| 6,573,275 B1 | 6/2003 | Urch et al. ............ 514/304 |
| 2002/0061913 A1 | 5/2002 | Urch et al. ............ 514/366 |

FOREIGN PATENT DOCUMENTS

| | | |
|---|---|---|
| EP | 0 545 099 | 6/1993 |
| EP | 0 589 301 | 3/1994 |
| JP | 63-48269 | 9/1988 |
| WO | 93/11117 | 6/1993 |
| WO | 02/08195 | 1/2002 |
| WO | 03/010149 | 2/2003 |

OTHER PUBLICATIONS

Heterocycles, vol. 29, No. 6, (month unavailable) 1989, pp. 1013-1016, Yoshinori Kondo et al, "Palladium-Catalyzed Indole and Benzofuran Ring Formation Accompanying Carbonylation".
J. Med. Chem., 39(4) (month unavailable) 1996, pp. 892-903, Lee F. Kuyper et al, "High-Affinity Inhibitors of Dihydrofolate Reductase: Antimicrobial and Anticancer Activities of 7,8-Dialkyl-1,3-diaminopyrrolo[3,2-f]quinazolines with Small Molecular Size".
Synthesis, Jun. 6, 1995, pp. 713-716, Micahael Harmata et al, "A General, Regioselective Synthesis of 2-Alkenylanilines".
Synthetic Communications, 24(2) (month unavailable) 1994, pp. 267-272, Maryam Hojjat et al, "An Activated Trifluoromethyl Group as a Novel Synthon for a Substituted Vinyl Function: Facil Synthesis of 2-(Substituted 1-Alkenyl)Anilines".
J. Am. Chem. Soc., 100, Jul. 19, 1978, pp. 4842-4852, Tsutomu Sugasawa et al, "Amino-haloborane in Organic Synthesis. 1. Specific Ortho Substitution Reaction of Anilines".
Synthesis (month unavailable) 1994, pp. 142-144, Michael Harmata et al, "A General, Regioselective Synthesis of 2-Alkylanilines".
Justus Liebigs Ann. Chem., 580 (month unavailable) 1953, pp. 44-57, Georg Wittig et al, "Zur Reaktionsweise des Pentaphenyl-phosphors und einiger Derivate".
Pure Appl. Chem., 9, (month unavailable) 1964, pp. 307-335, B.A. Arbusow, "Michaelis-Arbusow- Und Perkowreaktionen".

* cited by examiner

*Primary Examiner*—Golam M. M. Shameem
(74) *Attorney, Agent, or Firm*—Richard E. L. Henderson

(57) ABSTRACT

This invention relates to novel pyrazolylcarboxanilides of the formula (I)

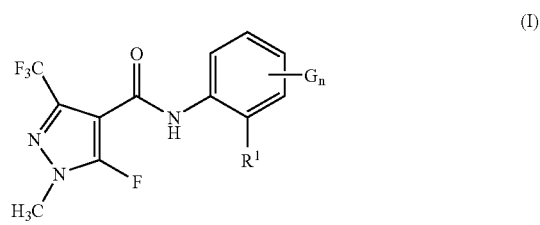

in which
$R^1$, G and n are as defined in the disclosure, to a plurality of processes for preparing these substances, to their use for controlling unwanted microorganisms, and to novel intermediates and their preparation.

11 Claims, No Drawings

PYRAZOLYL CARBOXANILIDES FOR CONTROLLING UNWANTED MICROORGANISMS

The present patent application has been filed under 35 U.S.C. 371 as a national stage application of PCT/EP2004/000344, filed Jan. 19, 2004, which was published in German as International Patent Publication WO 2004/067515 on Aug. 12, 2004, and is entitled to the right of priority of German Patent Application 103 03 589.3, filed Jan. 29, 2003.

The present invention relates to novel pyrazolycarboxanilides, to a plurality of processes for their preparation and to their use for controlling unwanted microorganisms.

There have now been found novel pyrazolylcarboxanilides of the formula (I)

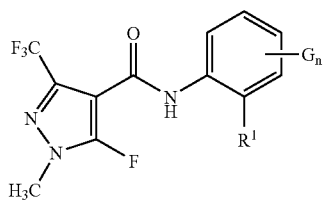

in which
R$^1$ represents unsubstituted $C_2$-$C_{20}$-alkyl or represents $C_1$-$C_{20}$-alkyl which is mono- or polysubstituted by identical or different substituents from the group consisting of halogen and $C_3$-$C_6$-cycloalkyl or represents $C_2$-$C_{20}$-alkenyl or $C_2$-$C_{20}$-alkynyl, each of which is optionally mono- or polysubstituted by identical or different substituents from the group consisting of halogen and $C_3$-$C_6$-cycloalkyl, where the cycloalkyl moiety for its part may optionally be mono- or polysubstituted by identical or different substituents from the group consisting of halogen and $C_1$-$C_4$-alkyl,
G represents halogen or $C_1$-$C_6$-alkyl,
n represents 0, 1 or 2.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers and the threo and erythro and also the optical isomers, any mixtures of these isomers and the possible tautomeric forms.

Furthermore, it has been found that pyrazolylcarboxanilides of the formula (I) are obtained when a) carboxylic acid derivatives of the formula (II)

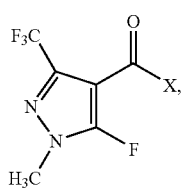

in which
X represents halogen,
are reacted with an aniline derivative of the formula (III)

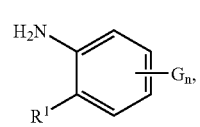

in which
R$^1$, G and n are as defined above,
if appropriate in the presence of an acid binder and if appropriate in the presence of a diluent, or b) pyrazolylcarboxanilides of the formula (Ia)

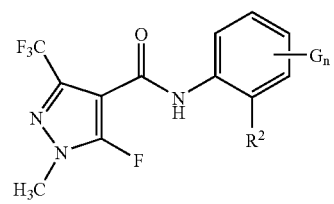

in which
G and n are as defined above and
R$^2$ represents $C_2$-$C_{20}$-alkenyl or $C_2$-$C_{20}$-alkynyl each of which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl
are hydrogenated, if appropriate in the presence of a diluent and if appropriate in the presence of a catalyst, or c) hydroxyalkylpyrazolylcarboxanilides of the formula (IV)

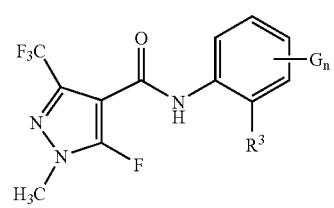

in which
G and n are as defined above and
R$^3$ represents $C_2$-$C_{20}$-hydroxyalkyl which is optionally additionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl
are dehydrated, if appropriate in the presence of a diluent and if appropriate in the presence of an acid, or d) halopyrazolylcarboxanilides of the formula (V)

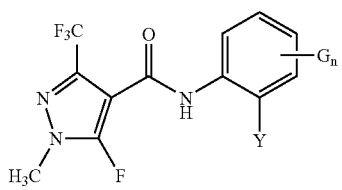

in which
G and n are as defined above and
Y represents bromine or iodine
are reacted with an alkyne of the formula (VI)

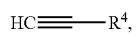

in which
$R^4$ represents $C_2$-$C_{18}$-alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl,
or an alkene of the formula (VII)

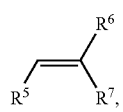

in which
$R^5$, $R^6$ and $R^7$ independently of one another each represent hydrogen or alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl and where the total number of carbon atoms of the open-chain moiety of the molecule does not exceed the number 20,
if appropriate in the presence of a diluent, if appropriate in the presence of an acid binder and in the presence of one or more catalysts, or
e) ketones of the formula (VIII)

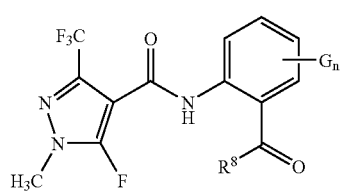

in which
G and n are as defined above and
$R^8$ represents hydrogen or $C_1$-$C_{18}$-alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl are reacted with a phosphorus compound of the general formula (IX)

$$R^9\text{-Px} \qquad (IX),$$

in which
$R^9$ represents hydrogen or $C_1$-$C_{18}$-alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl,
Px represents a grouping —$P^+(C_6H_5)_3$ $Cl^-$, —$P^+(C_6H_5)_3$ $Br^-$, —$P^{+(C}{_6}H_5)_3$ $I^{31}$, —$P(=O)(OCH_3)_3$ or —$P(=O)(OC_2H_5)_3$,
if appropriate in the presence of a diluent.

Finally, it has been found that the novel pyrazolylcarboxanilides of the formula (1) have very good microbicidal properties and can be used for controlling unwanted microorganisms both in crop protection and in the protection of materials.

Surprisingly, the pyrazolylcarboxanilides of the formula (I) according to the invention have considerably better fungicidal activity than the constitutionally most similar active compounds of the prior art having the same direction of action.

The formula (I) provides a general definition of the pyrazolylcarboxanilides according to the invention.

$R^1$ preferably represents unsubstituted $C_2$-$C_{12}$-alkyl or represents $C_1$-$C_{12}$-alkyl which is mono- to tetrasubstituted by identical or different substituents from the group consisting of fluorine, chlorine, bromine and $C_3$-$C_6$-cycloalkyl or represents $C_2$-$C_{12}$-alkenyl or $C_2$-$C_{12}$-alkynyl, each of which is optionally mono- to tetrasubstituted by identical or different substituents from the group consisting of fluorine, chlorine, bromine and $C_3$-$C_6$-cycloalkyl, where the cycloalkyl moiety for its part may optionally be mono- to tetrasubstituted by identical or different substituents from the group consisting of halogen and $C_1$-$C_4$-alkyl.

G preferably represents halogen or $C_1$-$C_6$-alkyl.

n preferably represents 0, 1 or 2.

$R^1$ particularly preferably represents ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl or decynyl, each of which is optionally mono- to tetrasubstituted by identical or different substituents from the group consisting of fluorine, cyclopropyl, difluorocyclopropyl, cyclobutyl, cyclopentyl and cyclohexyl and each of which is straight-chain or branched and each of which may be attached in any position.

G particularly preferably represents fluorine, chlorine, methyl, ethyl, t-butyl or 2,4-dimethylbutyl.

n particularly preferably represents 0, 1 or 2.

Very particular preference is furthermore given to compounds of the formula (I) in which $R^1$ represents unsubstituted $C_2$-$C_{20}$-alkyl (preferably $C_2$-$C_{12}$-alkyl, particularly preferably $C_2$-$C_6$-alkyl).

Very particular preference is furthermore given to compounds of the formula (I) in which
n represents 0.

Saturated or unsaturated hydrocarbon radicals, such as alkyl or alkenyl, can in each case be straight-chain or branched as far as this is possible, including the combination with heteroatoms, such as, for example, in alkoxy.

Optionally substituted radicals can be mono- or polysubstituted, where, in the case of polysubstitution, the substituents can be identical or different. A plurality of radicals having the same indices, such as, for example, n radicals G for n>1, can be identical or different.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. They apply both to the end products and, correspondingly, to precursors and intermediates.

The given definitions can be combined with one another as desired. Moreover, individual definitions may not apply.

Using 5-fluoro-1-methyl-3-(trifluoromethyl)pyrazole-4-carbonyl chloride and 2-(1-methylhexyl)aniline as starting materials, the process a) according to the invention can be illustrated by the formula scheme below:

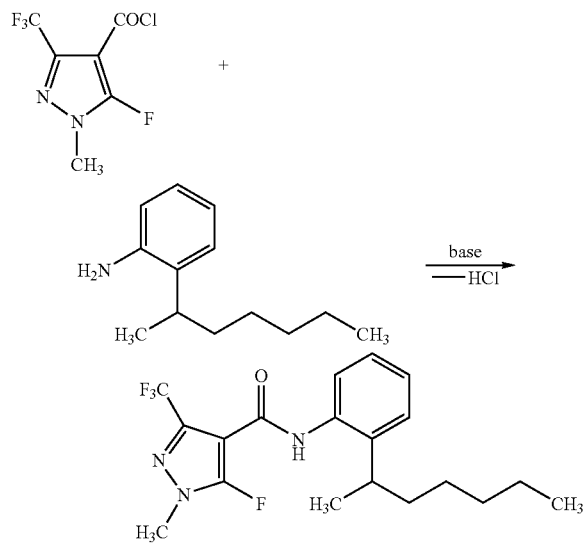

The formula (II) provides a general definition of the carboxylic acid derivatives required as starting materials for carrying out the process a) according to the invention. In this formula (II), X preferably represents chlorine.

The carboxylic acid derivatives of the formula (II) are known and/or can be prepared by known processes (cf. WO 93/11117, EP-A 0 545 099, EP-A 0 589 301 and EP-A 0 589 313).

The formula (III) provides a general definition of the anilines furthermore required as starting materials for carrying out the process a) according to the invention. In this formula (III), $R^1$, G and n preferably and particularly preferably have those meanings which have already been mentioned in connection with the description of the compounds of the formula (I) according to the invention as being preferred and particularly preferred, respectively, for these radicals.

The aniline derivatives of the formula (III) are known and/or can be prepared by known methods (cf., for example, Heterocycles (1989), 29(6), 1013-16; J. Med. Chem. (1996), 39(4), 892-903; Synthesis (1995), (6), 713-16; Synth. Commun. (1994), 24(2), 267-72; DE 2727416; Synthesis (1994), (2), 142-4; EP 0 824 099).

Using N-[2-((1Z)-1-methylhex-1-enyl)phenyl][5-fluoro-1-methyl-3-(trifluoro-methyl)pyrazol-4-yl] and hydrogen as starting materials and a catalyst, the course of the process b) according to the invention can be illustrated by the formula scheme below:

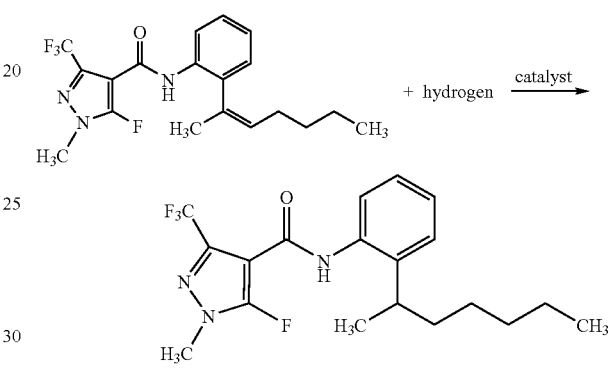

The formula (Ia) provides a general definition of the pyrazolylcarboxanilides required as starting materials for carrying out the process b) according to the invention. In this formula (Ia), G and n preferably and particularly preferably have those meanings which have already been mentioned in connection with the description of the compounds of the formula (I) according to the invention as being preferred and particularly preferred, respectively, for these radicals.

$R^2$ preferably represents $C_2$-$C_{12}$-alkenyl or $C_2$-$C_{12}$-alkynyl, each of which is optionally mono- to tetrasubstituted by identical or different substituents from the group consisting of fluorine, chlorine and $C_3$-$C_6$-cycloalkyl, where the cycloalkyl moiety for its part may optionally be mono- to tetrasubstituted by identical or different substituents from the group consisting of halogen and $C_1$-$C_4$-alkyl.

$R^2$ particularly preferably represents ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl or decynyl, each of which is optionally mono- to tetrasubstituted by identical or different substituents from the group consisting of fluorine, cyclopropyl, difluorocyclopropyl, cyclobutyl, cyclopentyl and cyclohexyl and each of which is straight-chain or branched and each of which may be attached in any position.

The compounds of the formula (Ia) are compounds according to the invention and can be prepared by process a), c), d) or e).

Using [5-fluoro-1-methyl-3-(trifluoromethyl)pyrazol-4-yl]-N-[2-(1-hydroxy-1-methylhexyl)phenyl]carboxamide as starting material and an acid, the course of the process c) according to the invention can be illustrated by the formula scheme below:

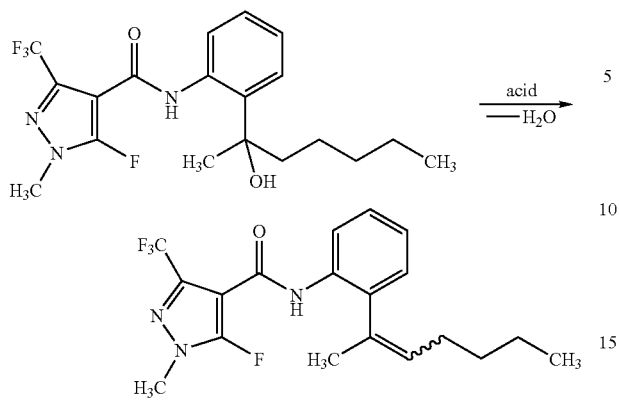

The formula (IV) provides a general definition of the hydroxyalkylpyrazolyl-carboxanilides required as starting materials for carrying out the process c) according to the invention. In this formula (IV), G and n preferably and particularly preferably have those meanings which have already been given in connection with the description of the compounds of the formula (I) according to the invention as being preferred and particularly preferred, respectively, for these radicals.

$R^3$ preferably represents $C_2$-$C_{12}$-hydroxyalkyl which is optionally additionally mono- to tetrasubstituted by identical or different substituents from the group consisting of chlorine, fluorine, bromine and $C_3$-$C_6$-cycloalkyl, where the cycloalkyl moiety for its part may optionally be substituted by halogen and/or $C_1$-$C_4$-alkyl.

$R^3$ particularly preferably represents hydroxyethyl, hydroxypropyl, hydroxybutyl, hydroxypentyl, hydroxyhexyl, hydroxyheptyl, hydroxyoctyl, hydroxynonyl or hydroxydecyl, each of which is optionally mono- to tetrasubstituted by identical or different substituents from the group consisting of fluorine, cyclopropyl, difluorocyclopropyl, cyclobutyl, cyclopentyl and cyclohexyl, each of which is straight-chain or branched and each of which may be attached in any position.

The compounds of the formula (IV) have hitherto not been disclosed and, as novel compounds, they also form part of the subject-matter of the present application.

It has also been found that the hydroxyalkylpyrazolylcarboxanilides of the formula (IV) have very good microbicidal properties and can be used for controlling unwanted microorganisms both in crop protection and in the protection of materials.

The hydroxyalkylpyrazolylcarboxanilides of the formula (IV) are obtained when f) carboxylic acid derivatives of the formula (II)

(II)

in which

X is as defined above, are reacted with a hydroxyalkylaniline derivative of the formula (X)

(X)

in which $R^3$, G and n are as defined above, if appropriate in the presence of an acid binder and if appropriate in the presence of a diluent.

Using 5-fluoro-1-methyl-3(trifluoromethyl)pyrazole-4-carbonyl chloride and 2-(2-aminophenyl)-2-heptanol as starting materials, the course of the process f) according to the invention can be illustrated by the formula scheme below:

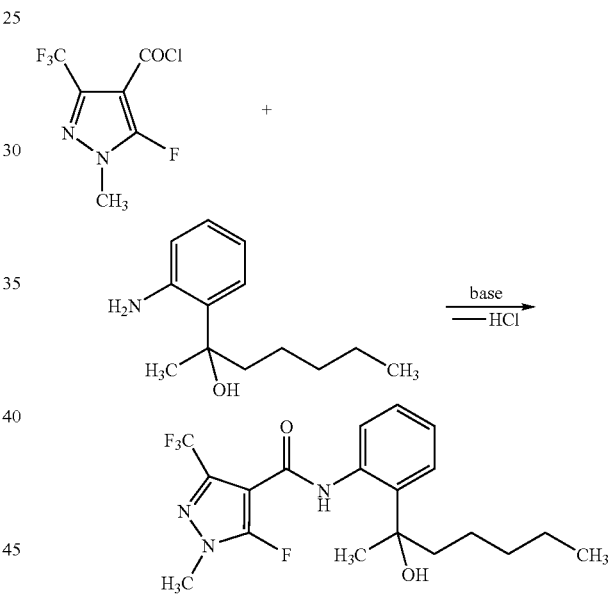

The carboxylic acid derivatives of the formula (II) required as starting materials for carrying out the process f) according to the invention have already been described further above, in connection with the description of the process a) according to the invention.

The formula (X) provides a general definition of the hydroxyalkylaniline derivatives furthermore required as starting materials for carrying out the process f) according to the invention. In this formula (X), $R^3$, G and n preferably and particularly preferably have those meanings which have already been given in connection with the description of the compounds of the formulae (I) and (IV) according to the invention as being preferred and particularly preferred, respectively, for these radicals.

The hydroxyalkylaniline derivatives of the formula (X) are known and/or can be obtained by known methods (cf., for example, U.S. Pat. No. 3,917,592 or EP 0 824 099).

Using [5-fluoro-1-methyl-3-(trifluoromethyl)pyrazol-4-yl]-N-(2-iodophenyl)carboxamide and 1-pentyne or, alternatively, 1-hexene as starting materials and in each case a catalyst and a base, the course of the process d) according to the invention can be illustrated by the two formula schemes below:

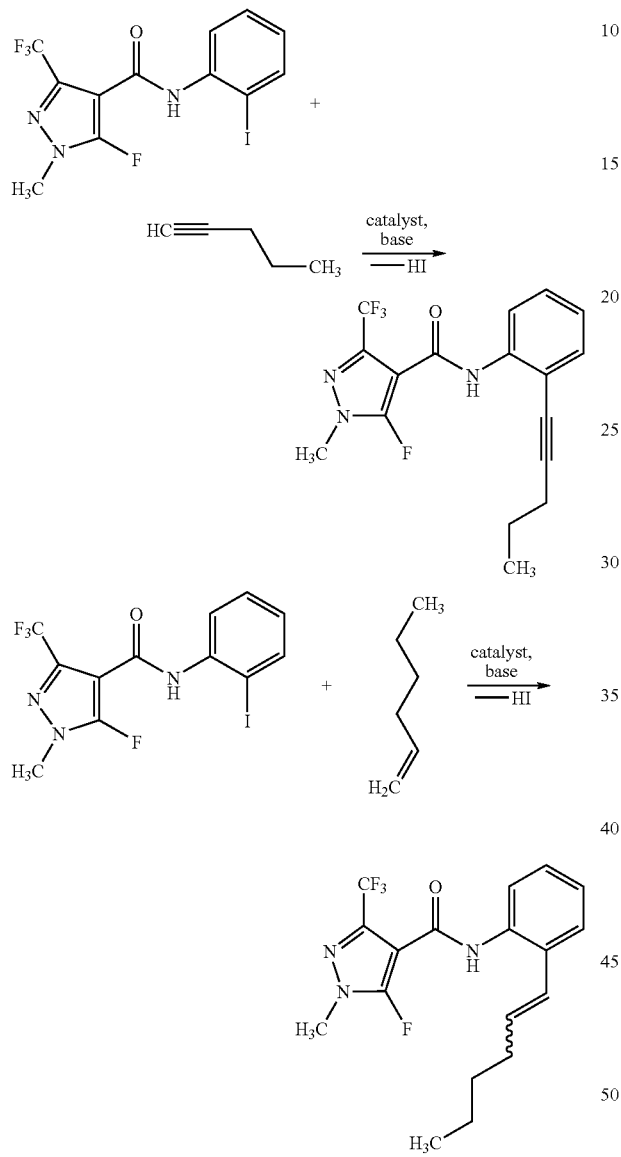

The formula (V) provides a general definition of the halopyrazolylcarboxanilides required as starting materials for carrying out the process d) according to the invention. In this formula (V), G and n preferably and particularly preferably have those meanings which have already been given in connection with the description of the compounds of the formula (I) according to the invention as being preferred and particularly preferred, respectively, for these radicals. Y preferably represents bromine or iodine.

The halopyrazolylcarboxanilides of the formula (V) have hitherto not been disclosed; as novel compounds, they also form part of the subject-matter of the present application.

They are obtained when
g) carboxylic acid derivatives of the formula (II)

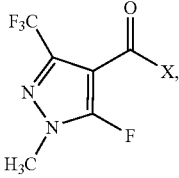

in which
X is as defined above,
are reacted with a haloaniline of the formula (XI)

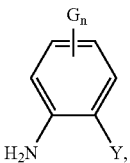

in which
G, n and Y are as defined above,
if appropriate in the presence of an acid binder and if appropriate in the presence of a diluent.

Using 5-fluoro-1-methyl-3-(trifluoromethyl)pyrazole-4-carbonyl chloride and 2-iodoaniline as starting materials, the course of the process g) according to the invention can be illustrated by the formula scheme below:

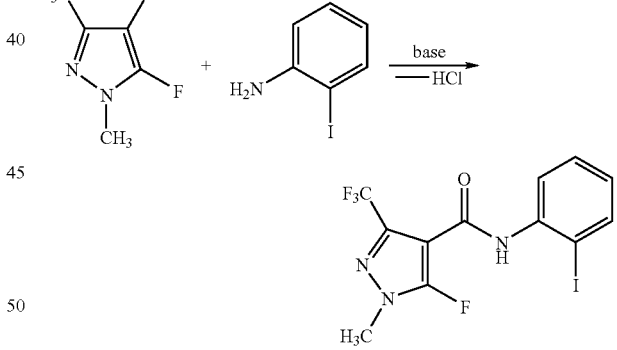

The carboxylic acid derivatives of the formula (II) required as starting materials for carrying out the process g) according to the invention have already been described further above, in connection with the description of the process a) according to the invention.

The formula (XI) provides a general definition of the haloanilines furthermore required as starting materials for carrying out the process g) according to the invention. In this formula (XI), G, n and Y preferably and particularly preferably have those meanings which have already been given in connection with the description of the compounds of the formulae (I) and (V) according to the invention as being preferred and particularly preferred, respectively, for these radicals.

The haloanilines of the formula (XI) are known chemicals for synthesis.

The formula (VI) provides a general definition of the alkynes furthermore required as starting materials for carrying out the process d) according to the invention.

- $R^4$ preferably represents $C_2$-$C_{10}$-alkyl which is optionally mono- to tetrasubstituted by identical or different substituents from the group consisting of fluorine, chlorine, bromine and $C_3$-$C_6$-cycloalkyl, where the cycloalkyl moiety for its part may optionally be substituted by halogen and/or $C_1$-$C_4$-alkyl.
- $R^4$ particularly preferably represents ethyl, propyl, butyl, pentyl, hexyl, heptyl or octyl, each of which is optionally mono- to tetrasubstituted by identical or different substituents from the group consisting of fluorine, cyclopropyl, difluorocyclopropyl, cyclobutyl, cyclopentyl and cyclohexyl, each of which is straight-chain or branched and each of which may be attached in any position.

The alkynes of the formula (VI) are known chemicals for synthesis.

The formula (VII) provides a general definition of the alkenes furthermore alternatively required as starting materials for carrying out the process d) according to the invention.

- $R^5$, $R^6$ and $R^7$ independently of one another preferably each represent hydrogen or alkyl which is optionally mono- to tetrasubstituted by identical or different substituents from the group consisting of fluorine, chlorine, bromine and $C_3$-$C_6$-cycloalkyl, where the cycloalkyl moiety for its part may optionally be substituted by halogen and/or $C_1$-$C_4$-alkyl and where the total number of carbon atoms of the open-chain moiety of the molecule does not exceed the number 12.
- $R^5$, $R^6$ and $R^7$ independently of one another particularly preferably each represent hydrogen or ethyl, propyl, butyl, pentyl, hexyl, heptyl or octyl, each of which is optionally mono- to tetrasubstituted by identical or different substituents from the group consisting of fluorine, cyclopropyl, difluorocyclopropyl, cyclobutyl, cyclopentyl and cyclohexyl, each of which is straight-chain or branched and each of which may be attached in any position, where the total number of the carbon atoms of the open-chain moiety of the molecule does not exceed the number 12.

The alkenes of the formula (VII) are known chemicals for synthesis.

Using N-(2-acetylphenyl)[5-fluoro-1-methyl-3-(trifluoromethyl)pyrazol-4-yl]carbox-amide and butyl(triphenyl)phosphonium iodide as starting materials, the course of the process e) according to the invention can be illustrated by the formula scheme below:

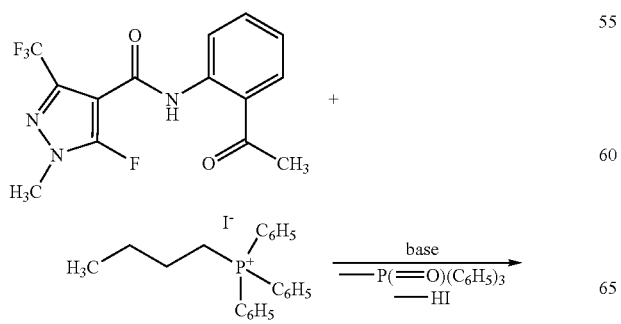

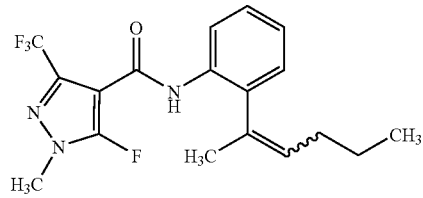

The formula (VIII) provides a general definition of the ketones required as starting materials for carrying out the process e) according to the invention. In this formula (VIII) and n preferably and particularly preferably have those meanings which have already been given in connection with the description of the compounds of the formula (I) according to the invention as being preferred and particularly preferred, respectively, for these radicals.

- $R^8$ preferably represents $C_2$-$C_{10}$-alkyl which is optionally mono- to tetrasubstituted by identical or different substituents from the group consisting of fluorine, chlorine, bromine and $C_3$-$C_6$-cycloalkyl, where the cycloalkyl moiety for its part may optionally be substituted by halogen and/or $C_1$-$C_4$-alkyl.
- $R^8$ particularly preferably represents ethyl, propyl, butyl, pentyl, hexyl, heptyl or octyl, each of which is optionally mono- to tetrasubstituted by identical or different substituents from the group consisting of fluorine, cyclopropyl, difluorocyclopropyl, cyclobutyl, cyclopentyl and cyclohexyl, each of which is straight-chain or branched and each of which may be attached in any position.

The ketones of the formula (VII) have hitherto not been disclosed. As novel chemical compounds, they also form part of the subject-matter of the present application.

They are obtained when h) carboxylic acid derivatives of the formula (II)

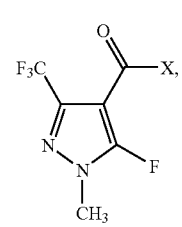

(II)

in which
X is as defined above,
are reacted with ketoanilines of the formula (XII)

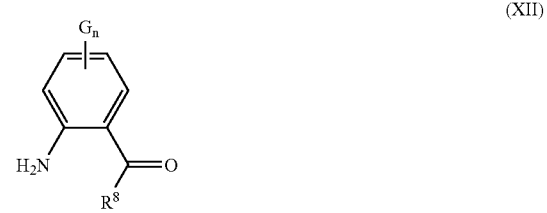

(XII)

in which

R[8], G and n are as defined above, if appropriate in the presence of an acid binder and if appropriate in the presence of a diluent.

Using 5-fluoro-1-methyl-3-(trifluoromethyl)pyrazole-4-carbonyl chloride and 1-(2-aminophenyl)ethanone as starting materials, the course of the process h) according to the invention can be illustrated by the formula scheme below:

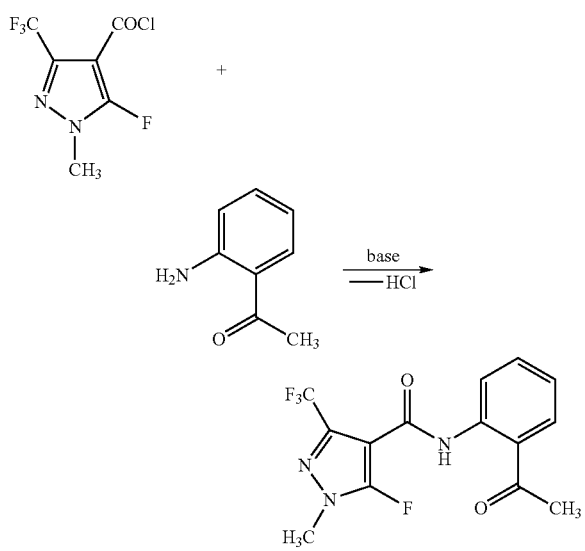

The carboxylic acid derivatives of the formula (II) required as starting materials for carrying out the process h) according to the invention have already been described further above, in connection with the description of the process a) according to the invention.

The formula (XII) provides a general definition of the ketoanilines furthermore required as starting materials for carrying out the process h) according to the invention. In this formula (XII), R[8], G and n preferably and particularly preferably have those meanings which have already been given in connection with the description of the compounds of the formulae (I) and (VIII) according to the invention as being preferred and particularly preferred, respectively, for these radicals.

The ketoanilines of the formula (XII) are generally customary chemicals for synthesis (compare, for example, J. Am. Chem. Soc. 1978, 100, 4842-4857 or U.S. Pat. No. 4,032,573).

The formula (IX) provides a general definition of the phosphorus compounds furthermore required as starting materials for carrying out the process e) according to the invention.

R[9] preferably represents $C_2$-$C_{10}$-alkyl which is optionally mono- to tetrasubstituted by identical or different substituents from the group consisting of chlorine, fluorine, bromine and $C_3$-$C_6$-cycloalkyl, where the cycloalkyl moiety for its part may optionally be substituted by halogen and/or $C_1$-$C_4$-alkyl.

R[11] particularly preferably represents ethyl, propyl, butyl, pentyl, hexyl, heptyl or octyl, each of which is optionally mono- to tetrasubstituted by identical or different substituents from the group consisting of fluorine, cyclopropyl, difluorocyclopropyl, cyclobutyl, cyclopentyl and cyclohexyl, each of which is straight-chain or branched and each of which may be attached in any position.

Px preferably represents a grouping $-P^+(C_6H_5)_3$ Cl$^-$, $-P^+(C_6H_5)_3$ Br$^{31}$, $-P^+(C_6H_5)_3$ I$^-$, $-P(=O)(OCH_3)_3$ or $-P(=O)(OC_2H_5)_3$.

The phosphorus compounds of the formula (IX) are known and/or can be prepared by known processes (compare, for example, Justus Liebigs Ann. Chem. 1953, 580, 44-57 or Pure Appl. Chem. 1964, 9, 307-335).

Suitable diluents for carrying out the processes a), f), g) and h) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxy-ethane or anisole, or amides, such as N,N-dimethylformamide, N,N-dimethyl-acetamide, N-methylformanilide, N-methylpyrrolidone or hexamethylphosphoric triamide.

The processes a), f), g) and h) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a), f), g) and h) according to the invention, the reaction temperatures can be varied within a relatively wide range. In general, the processes are carried out at temperatures of from 0° C. to 150° C., preferably at temperatures of from 0° C. to 80° C.

For carrying out the process a) according to the invention for preparing the compounds of the formula (I), in general from 0.2 to 5 mol, preferably from 0.5 to 2 mol, of aniline derivative of the formula (III) are employed per mole of the carboxylic acid derivative of the formula (II).

For carrying out the process f) according to the invention for preparing the compounds of the formula (IV), in general from 0.2 to 5 mol, preferably from 0.5 to 2 mol, of hydroxyalkylaniline derivative of the formula (X) are employed per mole of the carboxylic acid derivative of the formula (II).

For carrying out the process g) according to the invention for preparing the compounds of the formula (V), in general from 0.2 to 5 mol, preferably from 0.5 to 2 mol, of haloaniline of the formula (XI) are employed per mole of the carboxylic acid derivative of the formula (II).

For carrying out the process h) according to the invention for preparing the compounds of the formula (VIII), in general from 0.2 to 5 mol, preferably from 0.5 to 2 mol, of ketoaniline of the formula (XII) are employed per mole of the carboxylic acid derivative of the formula (II).

Suitable diluents for carrying out the process b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydro-furan, 1,2-dimethoxyethane, 1,2-diethoxyethane or anisole; or alcohols, such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether.

The process b) according to the invention is, if appropriate, carried out in the presence of a catalyst. Suitable catalysts are all catalysts customarily used for hydrogenations. The following may be mentioned by way of example: Raney nickel, palladium or platinum, if appropriate on a support, such as, for example, activated carbon.

Instead of in the presence of hydrogen in combination with a catalyst, the hydrogenation in process b) according to the invention can also be carried out in the presence of triethylsilane.

When carrying out the process b) according to the invention, the reaction temperatures can be varied within a relatively wide range. In general, the process is carried out at temperatures of from 0° C. to 150° C., preferably at temperatures of from 0° C. to 80° C.

Suitable diluents for carrying out the process c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydro-furan, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethyl-formamide, N,N-dimethylacetamide, N-methyl-formanilide, N-methylpyrrolidone or hexamethylphosphoric triamide; esters, such as methyl acetate or ethyl acetate; sulfoxides, such as dimethyl sulfoxide, sulfones, such as sulfolane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process c) according to the invention is, if appropriate, carried out in the presence of an acid. Suitable acids are all inorganic and organic protic acids and also Lewis acids, and also all polymeric acids. These include, for example, hydrogen chloride, sulfuric acid, phosphoric acid, formic acid, acetic acid, trifluoroacetic acid, methanesulfonic acid, trifluoromethanesulfonic acid, toluenesulfonic acid, boron trifluoride (also as etherate), boron tribromide, aluminum trichloride, titanium tetrachloride, tetrabutyl orthotitanate, zinc chloride, iron(III) chloride, antimony pentachloride, acidic ion exchangers, acidic aluminas and acidic silica gel.

When carrying out the process c) according to the invention, the reaction temperatures can be varied within a relatively wide range. In general, the process is carried out at temperatures of from 0° C. to 150° C., preferably at temperatures of from 0° C. to 80° C.

The processes c) and b) according to the invention can also be carried out in a tandem reaction ("one-pot reaction"). To this end, a compound of the formula (IV) is reacted, if appropriate in the presence of a diluent (suitable solvents as for process c)), if appropriate in the presence of an acid (suitable acids as for process c)) and in the presence of triethylsilane.

Suitable diluents for carrying out the process d) according to the invention are all inert organic solvents. These preferably include nitriles, such as acetonitrile, propionitrile, n- or i-butyronitrile or benzonitrile, or amides, such as N,N-dimethyl-formamide, N,N-dimethylacetamide, N-methyl-formanilide, N-methylpyrrolidone or hexamethylphosphoric triamide.

The process d) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as tri-methylamine, triethylamine, tributylamine, N,N-dimethylaniline, N,N-dimethyl-benzylamine, pyridine, N-methylpiperidine, N-methylnorpholine, N,N-dimethyl-aminopyridine, diazabicyclooctane (DABCO), diazabicyclononene (DBN) or diaza-bicycloundecene (DBU).

The process d) according to the invention is carried out in the presence of one or more catalysts.

Particularly suitable for this purpose are palladium salts or complexes. These are preferably palladium chloride, palladium acetate, tetrakis(triphenylphosphine)-palladium or bis (triphenylphosphine)palladium dichloride. It is also possible to generate a palladium complex in the reaction mixture by adding a palladium salt and a complex ligand separately to the reaction.

Suitable ligands are, preferably, organophosphorus compounds. The following may be mentioned by way of example: triphenylphosphine, tri-o-tolylphosphine, 2,2'-bis (diphenylphosphino)-1,1'-binaphthyl, dicyclohexylphosphinebiphenyl, 1,4-bis(diphenylphosphino)butane, bis-diphenylphosphinoferrocene, di(tert-butyl-phosphino) biphenyl, di(cyclohexylphosphino)biphenyl, 2-dicyclohexylphosphino-2'-N,N-dimethylaminobiphenyl, tricyclohexylphosphine, tri-tert-butylphosphine. However, it is also possible to dispense with ligands.

The process d) according to the invention is furthermore, if appropriate, carried out in the presence of a further metal salt, such as copper salts, for example copper(I) iodide.

When carrying out the process d) according to the invention, the reaction temperatures can be varied within a relatively wide range. In general, the process is carried out at temperatures of from 20° C. to 180° C., preferably at temperatures of from 50° C. to 150° C.

For carrying out the process d) according to the invention for preparing the compounds of the formula (I), in general from 1 to 5 mol, preferably from 1 to 2 mol, of alkyne of the formula (VI) or alkene of the formula (VII) are employed per mole of the halopyrazolylcarboxanilide of the formula (V).

Suitable diluents for carrying out the process e) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydro-furan, 1,2-dimethoxyethane, 1,2-diethoxyethane or anisole; nitriles, such as aceto-nitrile, propionitrile, n- or i-butyronitrile or benzonitrile; amides, such as N,N-di-methylformamide, N,N-dimethylacetamide, N-methylformanilide, N-methyl-pyrrolidone or hexamethylphosphoric triamide; esters, such as methyl acetate or ethyl acetate; sulfoxides, such as dimethyl sulfoxide; sulfones, such as sulfolane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether.

The process e) according to the invention is, if appropriate, carried out in the presence of a suitable acid acceptor. Suitable acid acceptors are all customary strong bases. These preferably include alkaline earth metal or alkali metal hydrides, hydroxides, amides, alkoxides or alkali metal hydrocarbon compounds, such as, for example, sodium hydride, sodium hydroxide, potassium hydroxide, sodium amide, lithium diisopropylamide, sodium methoxide, sodium ethoxide, potassium tert-butoxide, methyllithium, phenyllithium or butyllithium.

When carrying out the process e) according to the invention, the reaction temperatures can be varied within a relatively wide range. In general, the process is carried out at temperatures of from −80° C. to 150° C., preferably at temperatures of from −30° C. to 80° C.

For carrying out the process e) according to the invention for preparing the compounds of the formula (I), in general from 1 to 5 mol, preferably from 1 to 2 mol, of phosphorus compound of the formula (IX) are employed per mole of the ketone of the formula (VIII).

All processes according to the invention are generally carried out under atmospheric pressure. However, it is also possible to operate under elevated or reduced pressure—in general between 0.1 bar and 10 bar.

The compounds according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or
Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae; and
Pseudocercosporella species, such as, for example, Pseudocercosporella herpotrichoides.

The active compounds according to the invention also have very good fortifying action in plants. Accordingly, they can be used for mobilizing the defenses of the plant against attack by undesirable microorganisms.

In the present context, plant-fortifying (resistance-inducing) substances are to be understood as meaning those substances which are capable of stimulating the defense system of plants such that, when the treated plants are subsequently inoculated with undesirable microorganisms, they show substantial resistance to these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling cereal diseases, such as, for example, against *Pyrenophora* species, diseases in viticulture and in the cultivation of fruit and vegetables, such as, for example, against *Alternaria* and *Podosphaera* species.

The active compounds according to the invention are also suitable for increasing the yield of crops. In addition, they show reduced toxicity and are well tolerated by plants.

At certain concentrations and application rates, the active compounds according to the invention can also if appropriate be used as herbicides, for influencing plant growth and for controlling animal pests. If appropriate, they can also be used as intermediates and precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, and, in the case of propagation material, in particular in the case of seeds, also by applying one or more coats.

In the protection of materials, the substances according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms.

The active compounds according to the invention preferably act against fungi, in particular molds, wood-discoloring and wood-destroying fungi (Basidiomycetes), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc. The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following compounds:

Fungicides:
2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide;N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulfate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, teclof-talam, copper sulfate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avernectin, AZ-60541, azadirachtin, azamethiphos, azinphos-methyl, azin-phos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulfone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan,

*Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphen-thion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacrb, vamidothion, vaniliprole, verbutin, *Verticillium lecanii*, WL-108477, WL-40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2, 2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

A mixture with other known active compounds, such as herbicides, or with fertilizers and growth regulators, safeners or semiochemicals, is also possible.

In addition, the compounds of the formula (I) according to the invention also have very good antimycotic activity. They have a very broad antimycotic activity spectrum in particular against dermatophytes and yeasts, molds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defense of the plants against insects, arachnids, nematodes, and slugs and snails owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulfonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybean), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned include also the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula (I) or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

PREPARATION EXAMPLES

Example 1

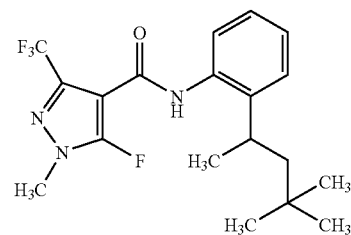

At from 0° C. to −10° C., a solution comprising 8.1 g (42.4 mmol) of 5-fluoro-1-methyl-3-(trifluoromethyl)pyrazole-4-carbonyl chloride in 80 ml of tetrahydrofuran is added dropwise to a solution comprising 6.5 g (28.3 mmol) of 2-(1,3,3-trimethylbutyl)phenylamine and 5.7 g (56.6 mmol) of triethylamine in 200 ml of tetrahydrofuran. The reaction mixture is stirred at 0° C. for 1 h. For work-up, the mixture is filtered through silica gel and concentrated. Purification on silica gel (petroleum ether/ethyl acetate 3:1) gives 10.1 g (94% of theory) of [5-fluoro-1-methyl-3-(trifluoromethyl)pyrazol-4-yl]-N-[2-(1,3,3-trimethylbutyl)phenyl]carbox-amide of log P (pH 2.3)=4.14.

The compounds of the formula (I) listed in table 1 below are obtained analogously to example 1 and in accordance with the statements in the general descriptions of the processes.

| Ex. No. | Compound | logP (pH 2.3) |
|---|---|---|
| 2 | ![structure] | 3.88 |
| 3 | ![structure] | 4.45 |

-continued

| Ex. No. | Compound | logP (pH 2.3) |
|---|---|---|
| 4 | (structure: pyrazole with F3C, N-N-CH3, F, carboxamide to phenyl with CH(CH3)CH2CH(CH3)2 group) | 4.27 |
| 5 | (structure: pyrazole with F3C, N-N-CH3, F, carboxamide to fluorophenyl with CH(CH3)CH2CH(CH3)2 group) | 3.92 |

The logP values given in the preparation examples and the tables above are determined in accordance with EEC Directive 79/831 Annex V.A8 by HPLC (High Performance Liquid Chromatography) on a reversed-phase column (C 18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-2-ones (having 3 to 16 carbon atoms) with known logP values (determination of the logP values by retention times using linear interpolation between two successive alkanones).

The lambda-max values were determined in the maxima of the chromatographic signals using the UV spectra from 200 nm to 400 nm.

USE EXAMPLES

Example A

*Puccinia* Test (Wheat)/Protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

TABLE A

*Puccinia* test (wheat)/protective

| Active compound according to the invention | Active compound application rate in g/ha | Efficacy in % |
|---|---|---|
| (structure: pyrazole-carboxamide with phenyl bearing CH(CH3)CH2C(CH3)3 group) | 500 | 100 |
| (structure: pyrazole-carboxamide with phenyl bearing CH(CH3)CH2CH(CH3)2 group) | 500 | 100 |

Example B

*Spaerotheca* Test (Cucumber)/Protective

| | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

TABLE B

*Spaerotheca* test (cucumber)/protective

| Active compound according to the invention | Active compound application rate in g/ha | Efficacy in % |
|---|---|---|
| (structure: F₃C-pyrazole-C(O)NH-phenyl with F, H₃C-N, H₃C, and CH(CH₃)CH₂C(CH₃)₃ substituent) | 100 | 100 |
| (structure: F₃C-pyrazole-C(O)NH-phenyl with F, H₃C-N, H₃C, and CH(CH₃)CH₂CH(CH₃)₂ substituent) | 100 | 100 |
| (structure: F₃C-pyrazole-C(O)NH-phenyl with F, H₃C-N, H₃C, and CH(CH₃)CH(H₃C)CH₂C(CH₃)₃ type substituent) | 100 | 98 |

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE C

*Venturia* test (apple)/protective

| Active compound according to the invention | Active compound application rate in g/ha | Efficacy in % |
|---|---|---|
| (structure: F₃C-pyrazole-C(O)NH-phenyl with F, H₃C-N, H₃C, and CH(CH₃)CH₂C(CH₃)₃ substituent) | 100 | 100 |
| (structure: F₃C-pyrazole-C(O)NH-phenyl with F, H₃C-N, H₃C, and CH(CH₃)CH₂CH(CH₃)₂ substituent) | 100 | 100 |
| (structure: F₃C-pyrazole-C(O)NH-phenyl with F, H₃C-N, H₃C, and CH(CH₃)CH(H₃C)CH₂C(CH₃)₃ type substituent) | 100 | 99 |

Example C

*Venturia* Test (Apple)/Protective

Example D

*Botrytis* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

Two days after the inoculation, the size of the infected areas on the leaves is evaluated. 0% means an efficacy which corresponds to that of the control, whereas an efficacy of 100% means that no infection is observed.

TABLE D

Botrytis test (bean)/protective

| Active compound according to the invention | Active compound application rate in g/ha | Efficacy in % |
|---|---|---|
| [structure: pyrazole-carboxanilide with F₃C, CH₃, F, H₃C-CH(CH₃)-CH₂-C(CH₃)₃ substituent] | 500 | 100 |
| [structure: pyrazole-carboxanilide with F₃C, CH₃, F, H₃C-CH(CH₃)-CH₂-CH(CH₃)₂ substituent] | 500 | 100 |
| [structure: pyrazole-carboxanilide with F₃C, CH₃, F, H₃C-CH(CH₃)-CH₂-C(CH₃)₂-CH₃ substituent] | 500 | 95 |

Example E

In Vitro Test for the ED$_{50}$ Determination in Microorganisms

A methanolic solution of the active compound to be tested, mixed with emulsifier PS16, is pipetted into the wells of a microtiter plate. After the solvent has evaporated, 200 µl of potato dextrose medium are added to each well.

Beforehand, a suitable concentration of spores or mycelium of the fungus to be tested was added to the medium.

The resulting concentrations of active compound are 0.1, 1, 10 and 100 ppm. The resulting concentration of the emulsifier is 300 ppm.

The plates are then incubated on a shaker at a temperature of 22° C. for 3-5 days, until sufficient growth can be observed in the untreated control.

Evaluation is carried out photometrically at a wavelength of 620 nm. The dose of active compound which causes 50% inhibition of fungal growth compared to the untreated control (ED$_{50}$) is calculated from data measured at different concentrations.

TABLE E

In vitro test for the ED$_{50}$ determination in microorganisms

| Active compound according to the invention | Microorganism | ED$_{50}$ value in ppm |
|---|---|---|
| [structure: pyrazole-carboxanilide with F₃C, CH₃, F, H₃C-CH(CH₃)-CH₂-C(CH₃)₃ substituent] | Alternaria mali | <0.1 |
| [structure: pyrazole-carboxanilide with F₃C, CH₃, F, H₃C-CH(CH₃)-CH₂-CH(CH₃)₂ substituent] | Alternaria mali | 0.28 |
| [structure: pyrazole-carboxanilide with F₃C, CH₃, F, H₃C-CH(CH₃)-CH₂-C(CH₃)₂-CH₃ substituent] | Alternaria mali | <0.1 |

What is claimed is:

1. A pyrazolylcarboxanilide of formula (I)

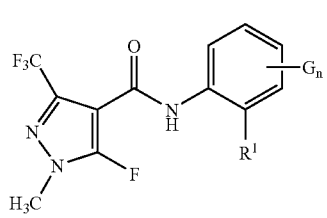

(I)

in which

R$^1$ represents unsubstituted C$_2$-C$_{20}$-alkyl; represents C$_1$-C$_{20}$-alkyl that is mono- or polysubstituted by identical or different substituents selected from the group consisting of halogen and $C_3$-$C_6$-cycloalkyl; or represents $C_2$-$C_{20}$-alkenyl or $C_2$-$C_{20}$-alkynyl, each of which is optionally mono- or polysubstituted by identical or different substituents selected from the group consisting of halogen and $C_3$-$C_6$-cycloalkyl, where the cycloalkyl moiety is optionally mono- or polysubstituted by identical or different substituents selected from the group consisting of halogen and $C_1$-$C_4$-alkyl, G represents halogen or $C_1$-$C_6$-alkyl, and n represents 0, 1, or 2.

2. The pyrazolylcarboxanilide of formula (I) according to claim 1 in which $R^1$ represents unsubstituted $C_2$-$C_{12}$-alkyl; represents $C_1$-$C_{12}$-alkyl that is mono- to tetrasubstituted by identical or different substituents selected from the group consisting of fluorine, chlorine, bromine, and $C_3$-$C_6$-cycloalkyl; or represents $C_2$-$C_{12}$-alkenyl or $C_2$-$C_{12}$-alkynyl, each of which is optionally mono- to tetrasubstituted by identical or different substituents selected from the group consisting of fluorine, chlorine, bromine, and $C_3$-$C_6$-cycloalkyl, where the cycloalkyl moiety is optionally mono- to tetrasubstituted by identical or different substituents selected from the group consisting of halogen and $C_1$-$C_4$-alkyl, G represents halogen or $C_1$-$C_6$-alkyl, and n represents 0, 1, or 2.

3. The pyrazolylcarboxanilide of formula (I) according to claim 1 in which $R^1$ represents ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl, or decynyl, each of which is optionally mono- to tetrasubstituted by identical or different substituents selected from the group consisting of fluorine, cyclopropyl, difluorocyclopropyl, cyclobutyl, cyclopentyl, and cyclohexyl and each of which is straight-chain or branched and each of which may be attached in any position, G represents fluorine, chlorine, methyl, ethyl, t-butyl, or 2,4-dimethylbutyl, n represents 0, 1, or 2.

4. The pyrazolylcarboxanilide of formula (I) according to claim 1 in which $R^1$ represents unsubstituted $C_2$-$C_{20}$-alkyl.

5. The pyrazolylcarboxanilide of formula (I) according to claim 1 in which $R^1$ represents unsubstituted $C_2$-$C_{12}$-alkyl.

6. The pyrazolylcarboxanilide of formula (I) according to claim 1 in which $R^1$ represents unsubstituted $C_2$-$C_6$-alkyl.

7. The pyrazolylcarboxanilide of formula (I) according to claim 1 in which n is 0.

8. A process for preparing compounds of formula (I) according to claim 1 comprising (a) reacting a carboxylic acid derivative of formula (II)

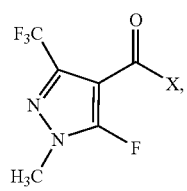

(II)

in which X represents halogen, with an aniline derivative of formula (III)

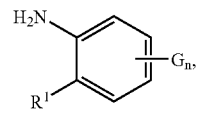

(III)

in which $R^1$, G, and n are as defined for formula (I) in claim 1; optionally in the presence of an acid binder and optionally in the presence of a diluent, or (b) hydrogenating a pyrazolylcarboxanilide of formula (Ia)

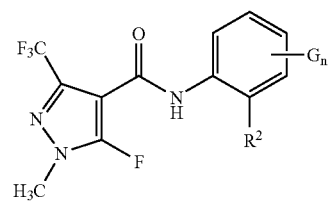

(Ia)

in which

G and n are as defined for formula (I) in claim 1, and $R^2$ represents $C_2$-$C_{20}$-alkenyl or $C_2$-$C_{20}$-alkynyl each of which is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl, optionally in the presence of a diluent and optionally in the presence of a catalyst, or (c) dehydrating a hydroxyalkylpyrazolylcarboxanilide of formula (IV)

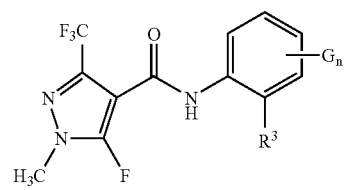

(IV)

in which

G and n are as defined for formula (I) in claim 1, and $R^3$ represents $C_2$-$C_{20}$-hydroxyalkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl optionally in the presence of a diluent and optionally in the presence of an acid, or (d) reacting a halopyrazolylcarboxanilide of formula (V)

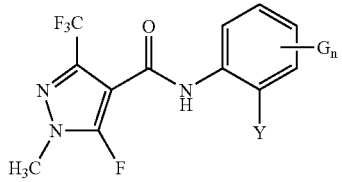

(V)

in which

G and n are as defined for formula (I) in claim 1, and Y represents bromine or iodine, with an alkyne of formula (VI)

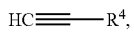

(VI)

in which $R^4$ represents $C_2$-$C_{18}$-alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl, or with an alkene of the formula (VII)

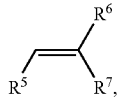

(VII)

in which $R^5$, $R^6$, and $R^7$ independently of one another each represent hydrogen or alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl and where the total number of carbon atoms of the open-chain moiety of the molecule does not exceed the number 20, optionally in the presence of a diluent, optionally in the presence of an acid binder, and in the presence of one or more catalysts, or (e) reacting a ketone of formula (VIII)

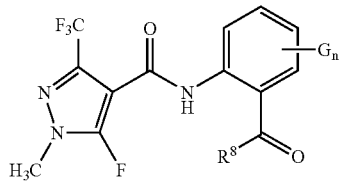

(VIII)

in which

G and n are as defined for formula (I) in claim 1, and $R^8$ represents hydrogen or $C_1$-$C_{18}$-alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl, with a phosphorus compound of formula (IX)

$$R^9\text{-Px} \qquad (IX),$$

in which $R^9$ represents hydrogen or $C_1$-$C_{18}$-alkyl that is optionally mono- or polysubstituted by identical or different substituents selected from the group consisting of halogen and $C_3$-$C_6$-cycloalkyl, where the cycloalkyl moiety is optionally substituted by halogen and/or $C_1$-$C_4$-alkyl, and Px represents a group —$P^+(C_6H_5)_3$ $Cl^-$, —$P^+(C_6H_5)_3$ $Br^-$, —$P^+(C_6H_5)_3$ $I^-$, —$P(=O)(OCH_3)_3$, or —$P(=O)(OC_2H_5)_3$, optionally in the presence of a diluent.

9. A composition for controlling unwanted microorganisms comprising one or more pyrazolylcarboxanilides of formula (I) according to claim 1 and one or more extenders and/or surfactants.

10. A method for controlling unwanted microorganisms comprising applying an effective amount of one or more pyrazolylcarboxanilides of formula (I) according to claim 1 to the microorganisms and/or their habitats.

11. A process for preparing compositions for controlling unwanted microorganisms comprising mixing one or more pyrazolylcarboxanilides of formula (I) according to claim 1 with one or more extenders and/or surfactants.

* * * * *